United States Patent [19]
Varner

[11] Patent Number: 5,471,980
[45] Date of Patent: Dec. 5, 1995

[54] TRACHEOSTOMY TUBE AND ORAL ENDOTRACHEAL TUBE HOLDER

[76] Inventor: Scott H. Varner, 1218 Rembrandt Cir., Charlotte, N.C. 28211

[21] Appl. No.: 251,283

[22] Filed: May 31, 1994

[51] Int. Cl.⁶ .................................................. A61M 16/00
[52] U.S. Cl. .............................. 128/207.17; 128/200.26
[58] Field of Search .................... 128/200.26, 207.14, 128/207.16, 207.17, 911, 912, DIG. 23, DIG. 26

[56] References Cited

U.S. PATENT DOCUMENTS

| | | | |
|---|---|---|---|
| 3,924,636 | 12/1975 | Addison | 128/207.14 |
| 4,313,437 | 2/1982 | Martin | 128/207.17 |
| 4,326,515 | 4/1982 | Shaffer et al. | 128/207.17 |
| 4,331,144 | 5/1982 | Wapner | 128/207.17 |
| 4,548,200 | 10/1985 | Wapner | 128/207.17 |
| 4,658,813 | 4/1987 | Jones | 128/207.14 |
| 4,717,385 | 6/1988 | Cameron et al. | 128/DIG. 26 |
| 4,817,598 | 4/1989 | LaBombard | 128/207.14 |
| 5,009,227 | 4/1991 | Nieuwstad | 128/207.14 |
| 5,146,913 | 9/1992 | Khorsandian et al. | 128/207.14 |
| 5,352,211 | 10/1994 | Merskelly | 128/DIG. 26 |

*Primary Examiner*—Edgar S. Burr
*Assistant Examiner*—V. Srivastava
*Attorney, Agent, or Firm*—Shefte, Pinckney & Sawyer

[57] ABSTRACT

A device for supporting and retaining a tracheostomy tube or an endotracheal tube in operational patient contact includes a support strap, a tube support member having an opening formed therein and at least one resilient tube engagement member projecting into the tube receiving opening for contacting and frictionally retaining a tube in the opening.

8 Claims, 2 Drawing Sheets

TRACHEOSTOMY TUBE AND ORAL ENDOTRACHEAL TUBE HOLDER

BACKGROUND OF THE INVENTION

The present invention relates in general to securing tracheostomy tubes and oral endotracheal tubes. More particularly, the present invention relates to a device for retaining such a tube in operational, patient contact.

Prior to 1983, the only method being used to any extent to secure a tracheostomy tube was strips of cotton fabric split at either end and then tied through the openings in the flange of the trache. Although reliable, it was extremely time consuming and tended to fray at the ends and roll up in a rope configuration which caused irritation to the patients neck. Wapner U.S. Pat. No. 4,331,144 addressed these problems.

Wapner U.S. Pat. No. '144 discloses a band which encircles the head and secures to itself using a hook and loop fastener. It also employs strips which thread through the slits in a trache flange and then secures back onto itself using hook and loop fasteners. This device currently is the only apparently viable arrangement available for securing a tracheostomy tube, other than the previously mentioned cotton strips.

while certainly functional, the Wapner device is also time consuming and can be extremely difficult to employ if the flange of the trache holder is pulled into folds of flesh as is often the case with overweight patients. To overcome this problem, the inward force normally required to hold the trache tube within the trachea must be reduced in order to allow the flanges to ride above the flesh folds. This scenario can result in the trache tube actually coming out of the stoma in the trachea.

In regards to securing oral endotracheal tubes, the generally practiced method is to use tape which is wrapped around a patient's neck and is then wrapped around the tube itself before being adhered to a patient's cheek for anchoring purposes. This technique is also time consuming and the tape needs to be replaced frequently due to saliva and blood which decreases the adhesive ability of the tape.

Addison U.S. Pat. No. 3,924,636 and Wapner U.S. Pat. No. 4,548,200 illustrate attempts to standardize and simplify the securing of oral endotracheal tubes. Addison U.S. Pat. No. '636 discloses a plastery with a central opening and a holding strap that is self-adhering. Wapner U.S. Pat. No. '200 discloses a device which employs a hook and loop fastener with adhesive backing which encircles the patient's head.

The Addison device, since it can stick to the patient's face by means of an adhesive plastery, cannot be used if the patient has any type of facial injury since it cannot be taped over a wound site, and the elliptical central opening does not prevent any lateral tube migration. Further, this device is not applicable to a tracheostomy tube.

In Wapner U.S. Pat. No. '200, since it employs a soft material in the region of the mouth, the tube holder would become stained and slippery in short order and would necessitate frequent replacement. It also is not applicable to tracheostomy tubes.

The present invention overcomes heretofore outstanding deficiencies existent in the state-of-the-art, as outlined above.

SUMMARY OF THE INVENTION

It is accordingly an object of the present invention to provide a device for supporting and retaining a tracheostomy tube or an endotracheal tube which may be used with both types of tubes and does not adhere to the patient's face so that it can be used for patients with facial injuries.

It is another object of the present invention to provide a device for supporting and retaining a tracheostomy tube or an endotracheal tube which provides non-fabric, moldable non-porous material for use in the vicinity of the mouth for oral endotracheal tube applications which is not susceptible to degradation or staining.

It is another object of the present invention to provide such a device which frictionally retains the tube, thereby eliminating the need for strips that are inserted through openings in a flange for tracheostomy tube applications, thereby enhancing the ease of use of the present invention.

To that end, a device for supporting and retaining a tracheostomy tube or an endotracheal tube in operational patient contact includes a generally elongate support strap for attachment to a patient and an assembly for supporting a tube mounted to the strap and including a body having a tube receiving opening formed therein and at least one resilient tube engagement member projecting into the tube receiving opening for contacting and frictionally retaining a tube in the opening.

It is preferred that the support assembly include a round opening and a plurality of tube engagement members projecting into the opening. Further, the strap may include an arrangement for retaining the strap on the patient. Preferably, the strap includes two end portions and the retaining arrangement includes a hook and loop fastener attached to the end portions.

Preferably, the tube itself includes an integral tube support flange and the tube support assembly includes a generally flat body having the tube receiving opening formed therein with the body conforming substantially to external dimensions of the tube support flange associated with the tube.

By the above, the present invention provides a simple and effective device for holding a tracheostomy or endotracheal tube in operational patient contact which both enhances the ease of use and the operational stability of either type of tube.

DETAILED DESCRIPTION OF THE PREFERRED EMBODIMENT

Figure 1:
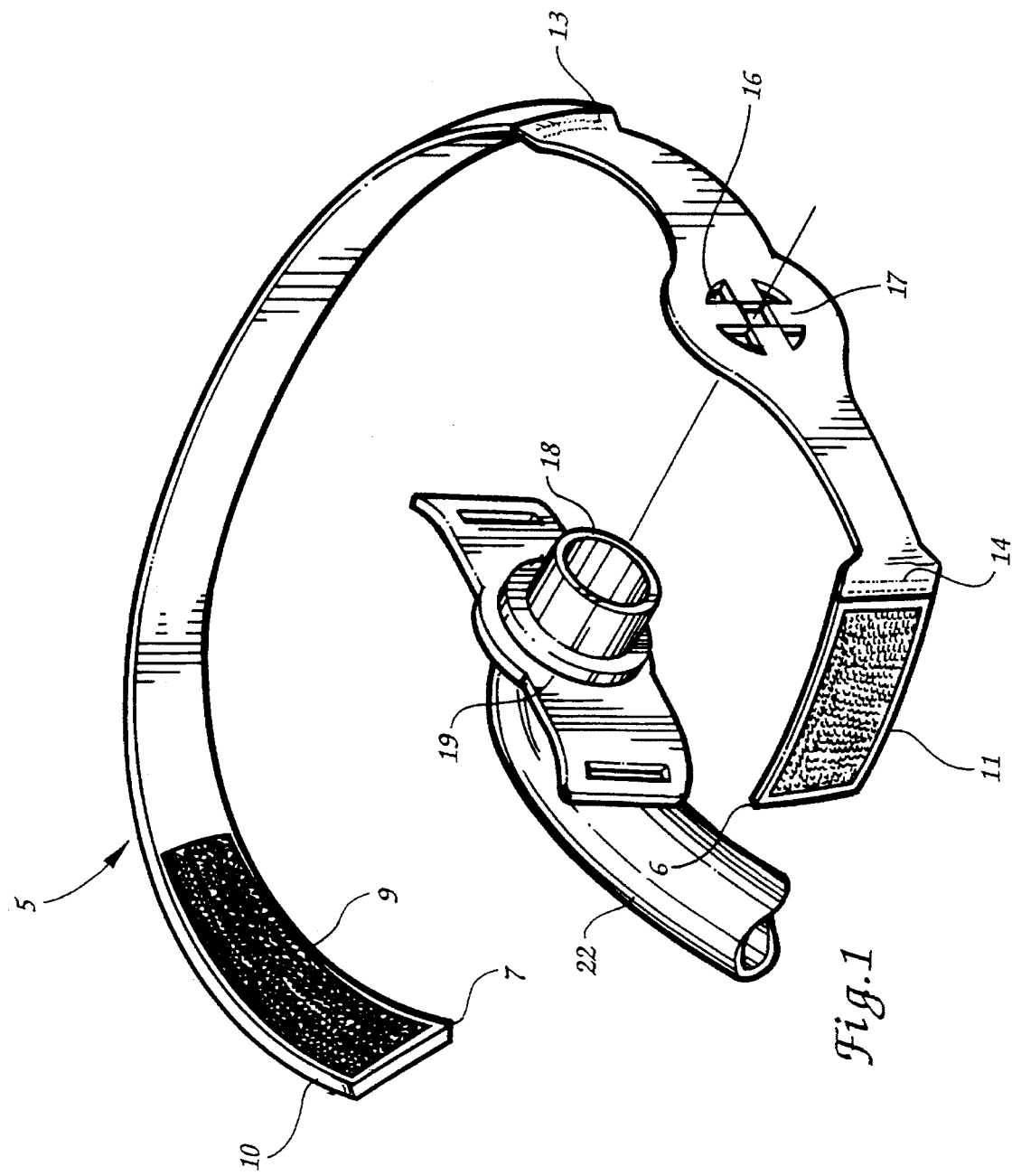
FIG. 1 is an exploded view of a device for supporting and retaining a tracheostomy or an endotracheal tube in operational patient contact constructed in accordance with the preferred embodiment of the present invention shown securing a tracheostomy tube.

Turning now to the drawings and, more particularly to FIG. 1, a device for supporting and retaining a tracheostomy tube or an endotracheal tube in operational patient contact is illustrated generally at 5 and includes a main body portion 15 having two straps 10,11 attached thereto. The body portion 15 is a generally flat, elongate flexible member, preferably formed of plastic and includes two end portions 13,14. A tube receiving opening 16 is formed at approximately the midpoint of the main body 15 and is generally circular in configuration. The main body 15 includes rounded edges generally corresponding to the curvature of the tube receiving opening 16.

Figure 2:
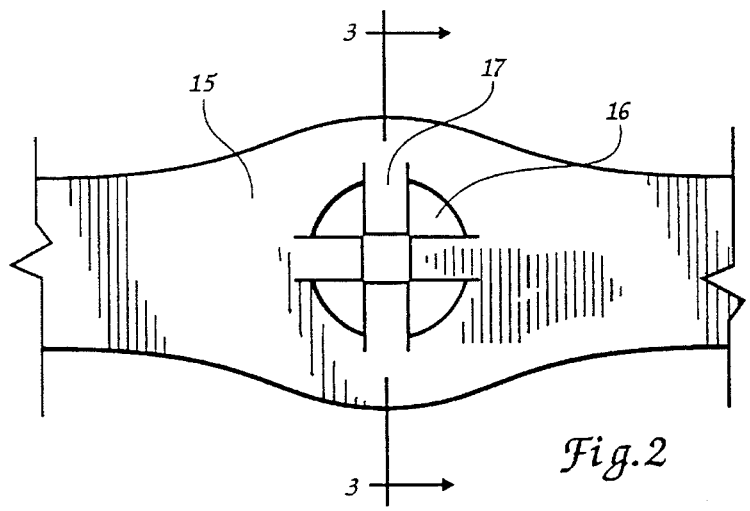
FIG. 2 is a front elevation view of the device illustrated in FIG. 1.

As best seen in FIG. 2 four tube engagement members 17 are formed into the main body portion 15 adjacent the opening 16 and arranged to project thereinto at 90° intervals. The tube engagement members 17 are generally rectangular members which form flexible, resilient fingers to frictionally grip and retain a endotracheal tube or a tracheostomy tube as will be seen in greater detail hereinafter.

A first strap 10 is attached to the main body 15 at the first end portion 13 and is foiled of a flexible, soft material. A first portion 9 of a hook and loop fastener is mounted to the distal end 17 of the first strap 10. A second strap 11 is attached to the main body 15 and a second end portion 6 projects outwardly therefrom. A second portion 8 of a hook and loop fastener is fixed to the outer face of the second strap 11. The second strap 11 is typically formed from the same material as the first strap 10. It should be noted that the first strap 10 is substantially longer than the second strap 11 so that the fastening of the first portion 9 of the hook and loop fastener with the second portion 8 of the hook and loop fastener can occur adjacent the front side of a patent which provides easier access for medical personnel.

It is preferred that the body portion 15 be formed of a moldable, non-porous material such as urethane, vinyl, or plastic. The main body 15 is approximately the same size and configuration as a flange 19 formed integrally with the tracheostomy tube 22. The tube receiving opening 16 is slightly larger than the outside diameter of the barrel 18 of the tracheostomy tube 22 to properly receive the barrel 18 therein, as seen in FIG. 1.

When retaining a tracheostomy tube 22, and with continued reference to FIG. 1, the tube receiving opening 16 is moved over the barrel 18 of the tracheostomy tube 22 until the main body portion 15 is flush with the surface of the flange 19 associated with the tracheostomy tube 22. The first strap 10 is then moved around the patient's neck and secured to the second strap 8 using the first and second hook and loop fastener portions 8,9. Inwardly directed pressure along the surface of the tube flange 19 from the device 10 retains the tracheostomy tube 22 in place.

Figure 3:
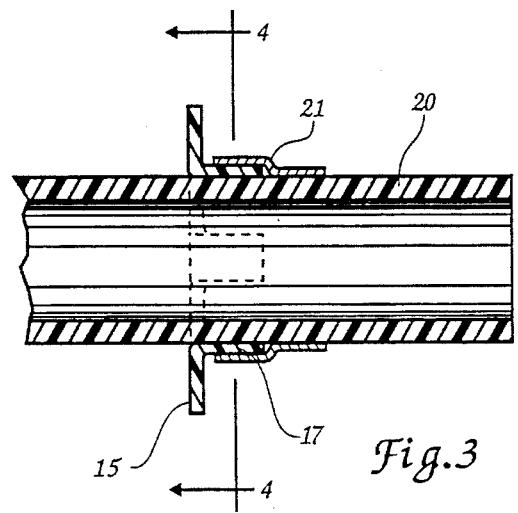
FIG. 3 is a fragmentary side view of the device illustrated in FIG. 1 securing an oral endotracheal tube and taken along line 3—3 of FIG. 2.
Figure 4:
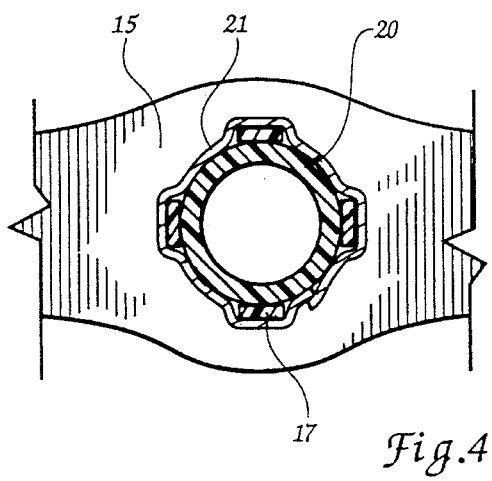
FIG. 4 is a front elevation of the device illustrated in FIG. 1 securing an oral endotracheal tube and taken along line 4—4 of FIG. 3.

With reference to FIGS. 3 and 4, the tube receiving opening 16 and the main body portion 15 is moved over a proximal end of the endotracheal tube 20 and moved down the tube 20 to the desired location, i.e., adjacent the patient's mouth. The tube engagement members 17 are bent 90° by the tube and lie flat against it. The tube engagement members, 17 are then secured to the tube by wrapping a narrow, non-cloth tape 21 around the perimeter of the tube in surrounding relationship with the flanges 17. This prevents any horizontal movement of the tube 20. The device may then be secured to the patient's neck as previously described.

While the present invention is illustrated and described using a round opening, it should understood that virtually any shaped opening can be employed without departing from the spirit and scope of the present invention. Similarly, while the device as illustrated and describe herein includes four uniformly rectangularly-shaped tube engagement members, the tube engagement members may be of virtually any number and configuration without departing from the spirit and scope of the present invention.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A device for supporting and retaining a tracheostomy tube or an endotracheal tube in operational patient contact comprising:

a generally elongate support strap for attachment to a patient; and means for supporting a tube mounted to said strap and including a body having a tube receiving opening formed therein and a plurality of resilient tube engagement members projecting into said tube receiving opening for contacting and frictionally retaining a tube in said opening.

2. A device according to claim 1 wherein said tube support means includes a round opening.

3. A device according to claim 1 wherein said support strap includes means for retaining said strap on the patient.

4. A device according to claim 1 wherein said strap includes two end portions and said retaining means includes a hook-and-loop fastener attached to said end portions.

5. A device according to claim 1 wherein the tube includes an integral tube support flange and said tube support means includes a generally flat body having said tube receiving opening formed, therein, said body conforming substantially to external dimension of the tube support flange.

6. A device for supporting and retaining a tracheostomy tube or an endotracheal tube .in operational patient contact comprising:

a generally elongate support strap;

a tube support member attached to said support strap, said tube support member including a generally flat elongate body having a tube receiving opening formed therein; and a plurality of tube engagement members formed circumferentially around said tube receiving opening and projecting a predetermined distance thereinto for engaging and frictionally retaining a tube within said tube receiving opening.

7. A device according to claim 6 wherein said support strap includes means for retaining said strap on the patient.

8. A device according to claim 6 wherein said strap includes two end portions and said retaining means includes a hook-and-loop fastener attached to said end portions.

* * * * *

UNITED STATES PATENT AND TRADEMARK OFFICE
CERTIFICATE OF CORRECTION

PATENT NO. : 5,471,980

DATED : December 5, 1995

INVENTOR(S) : Scott H. Varner

It is certified that error appears in the above-identified patent and that said Letters Patent is hereby corrected as shown below:

Column 1, line 9,

In the Background of the Invention, line 5 (not including heading), delete "1983" and insert therefor -- 1982 --.

Column 1, line 25, delete "while" and insert therefor -- While --.

Column 3, line 7, after "FIG. 2" insert -- , --.

Column 3, line 15, delete "foiled" and insert therefor -- formed --.

Column 3, lines 52-53, after "members" delete ",".

Column 4, line 45, after "formed" delete ",".

Signed and Sealed this

Eighteenth Day of June, 1996

Attest:

BRUCE LEHMAN

*Attesting Officer*   *Commissioner of Patents and Trademarks*